United States Patent [19]

Ashina et al.

[11] Patent Number: 4,485,261

[45] Date of Patent: Nov. 27, 1984

[54] PROCESS FOR PRODUCING METHYLAMINES

[75] Inventors: Yoshiro Ashina, Zushi; Michio Fukatsu, Yokohama, both of Japan

[73] Assignee: Nitto Kagaku Kogyo Kabushiki Kaisha, Tokyo, Japan

[21] Appl. No.: 367,022

[22] Filed: Apr. 9, 1982

[30] Foreign Application Priority Data

Apr. 10, 1981 [JP] Japan .................................. 56-53888

[51] Int. Cl.$^3$ .......................................... C07C 85/02
[52] U.S. Cl. ..................................... 564/479; 564/486
[58] Field of Search ............................... 564/476, 486

[56] References Cited

U.S. PATENT DOCUMENTS

| | | | |
|---|---|---|---|
| Re. 19,632 | 7/1935 | Arnold | 564/479 |
| 3,384,667 | 5/1968 | Hamilton | 564/447 |
| 3,387,032 | 6/1968 | Leonard | 564/479 |
| 3,694,378 | 9/1972 | Ebregi | 252/455 Z |
| 4,191,709 | 3/1980 | Parker et al. | 252/455 Z |
| 4,205,012 | 5/1980 | Parker et al. | 252/455 Z |
| 4,209,498 | 6/1980 | Whittman | 252/431 N |
| 4,217,240 | 8/1980 | Bergna | 252/455 R |

*Primary Examiner*—William R. Dixon, Jr.
*Assistant Examiner*—Margaret B. Medley
*Attorney, Agent, or Firm*—Robert E. Burns; Emmanuel J. Lobato; Bruce L. Adams

[57] ABSTRACT

Methylamines rich in dimethylamine are produced through two-step reaction of ammonia and methanol in which two types of catalysts are used and the methylamine mixture produced is recycled to the first step reaction.

10 Claims, 3 Drawing Figures

PROCESS FOR PRODUCING METHYLAMINES

BACKGROUND OF THE INVENTION

1. Field of the Art

The present invention relates to a process for producing methylamines by a gas phase catalytic reaction of methyl alcohol with ammonia. More particularly, the present invention relates to a process for producing methylamines characterized in that the catalytic reaction is carried out in two steps by using different catalysts.

Methylamines are usually prepared by reacting methanol with ammonia in gas phase in the presence of a solid acid catalyst (hereinafter referred to as conventional catalyst) such as alumina and silica at an elevated temperature. In this catalytic reaction, part or all of the hydrogen atoms in the ammonia are replaced with a methyl group, whereby three types of methylamines, i.e., monomethylamine (hereinafter referred to as MMA), dimethylamine (hereinafter referred to DMA) and trimethylamine (hereinafter referred to as TMA) are simultaneously produced. These methylamines are separated from the reaction mixture. DMA which is in greatest commercial demand among these methylamines is utilized as a final product, while MMA and TMA which are in less commercial demand are mostly transferred to the reaction system for reuse. In this case, the methylamine mixture (MMA+TMA) transferred to the reaction system contains the non-reacted ammonia because an excessive amount of ammonia is usually used in order to enhance the equilibrium conversion of methanol and the production ratio of DMA during the catalytic reaction. Therefore, it may be stated as a conclusion that methylamines are prepared by reacting together methanol, ammonia and a methylamine mixture containing TMA.

DMA is separated from the reaction product by distillation. However, it is not easy to distill DMA. Since TMA contained in the reaction product forms azeotropic mixtures with ammonia, other amines and the non-reacted methanol, respectively, recovery of DMA or a DMA-TMA azeotropic mixture, recovery of DMA from the DMA-TMA azeotropic mixture, and recovery of MMA and TMA become necessary, which unavoidably causes the operation to be complicated, the apparatus to be large-sized, and the consumption of energy to be increased.

Accordingly, if the formation of DMA is promoted in the synthetic reaction system while the formation of TMA is suppressed, reduction in the utility cost of the DMA refining process and decrease in the size of the apparatus can be directly attained.

However, the final ratios of formation for three types of methylamines are thermodynamically determined. That is, the higher the temperature and the higher the ratio of the number of nitrogen atoms to the number of carbon atoms, N/C, in the reaction mixture, the higher is the ratio of formation of DMA and the lower is the ratio of formation of TMA. For example, when the reaction temperature is 400° C. and the N/C is 2.0, the ratio of formation at equilibrium of each methylamine is thermodynamically calculated as follows: MMA=0.288, DMA=0.279 and TMA=0.433. Since the rate of formation of TMA is relatively high in the presence of the conventional catalyst, the ratio of formation of DMA or the ratio of formation of DMA/TMA never exceeds the above mentioned equilibrium value throughout the reaction process. Therefore, a large amount of TMA and MMA after they are separated from the reaction product should be recycled to the reaction system as described hereinabove. The ratio of formation of DMA can be increased by increasing the reaction temperature or the N/C ratio so as to shift the reaction equilibrium itself. In this case, however, the increase in the reaction temperature results in an increase in the formation of impurities and the increase in the N/C ratio causes the non-reacted ammonia to be recycled to be increased, which requires a large-sized apparatus. For these reasons, these approaches are not always advantageous from an economic point of view.

PRIOR ART

For producing mono-substituted and di-substituted amines in an amount greater than that of a tri-substituted amine, U.S. Pat. No. 3,384,667 discloses a method for reacting an alcohol with ammonia on a dehydrated crystalline aluminosilicate having pores of such a size as to allow the mono- and di-substituted amines to pass therethrough, but not the tri-substituted amine.

U.S. Pat. Nos. 4,191,709, 4,205,012 and 4,209,498 disclose Zeolite FU-1 which was synthesized by a special method as a catalyst for use in the gas phase catalytic reaction of methyl alcohol with ammonia.

We have previously proposed one solution to the production of DMA in a yield higher than the thermodynamic equilibrium value from the point of view of the catalyst. The proposed catalyst consisted of a mordenite type zeolite. It is considered that when this catalyst is used, the TMA molecules having the highest size among the reactants are prevented from being separated from within the pores of the zeolite due to the steric hindrance of the pore entrance (the mordenite type zeolite has an effective pore size of about 5 Å which is greatly different from the average pore size of 20 Å or more of the conventional catalyst), whereby the reaction of formation of TMA is suppressed and the selectivity for DMA is increased. For example, when a mixture of ammonia and methanol in equal quantity is reacted together under the reaction conditions of a temperature of 400° C., a pressure of 20 atmospheres, and a space velocity of 2500, the conventional catalyst gives a conversion of methanol of 98%, a ratio of DMA formation of 0.270, and a ratio of TMA formation of 0.445 based on the total weight of the three amines, which ratios can almost equal to the thermodynamic equilibrium values, while the mordenite type zeolite gives a conversion of methanol of 97%, a ratio of DMA formation of 0.349, and a ratio of TMA formation of 0.304. As is apparent from the above mentioned results, in the case of the mordenite type zeolite, the amount of TMA produced is remarkably reduced and the selectivity for DMA is remarkably increased.

Although this type of catalyst is effective for suppressing the reaction of formation of TMA due to the blocking action of the pore entrance, it is natural that the catalyst simultaneously suppresses the reaction of consumption of the supplied TMA. Therefore, when this catalyst is directly applied to a conventional industrial apparatus wherein an operation for recycling TMA is carried out, the TMA recycled to the reaction system is not substantially converted to DMA and remains as it is, with the consequence that a specific effect of this catalyst of a low selectivity for TMA and a high selectivity for DMA can not be obtained to a satisfactory extent.

SUMMARY OF THE INVENTION

An object of the present invention is to overcome the above described difficulties encountered heretofore.

The object of the present invention can be attained by carrying out the above mentioned catalytic reaction in two stages using, different catalysts with respect to the reaction of TMA.

The process for producing methylamines according to the present invention, wherein methanol, ammonia and a methylamine mixture containing trimethylamine are subjected to a gas-phase catalytic reaction, is characterized by a combination of a first step and a second step, the first step comprising subjecting all or part of the methylamine mixture and all or part of the ammonia and, if necessary, part of the methanol to a catalytic reaction to reduce the amount of the trimethylamine, and the second step comprising subjecting all or part of the product resulting from the first step, methanol and the remaining ammonia and, if necessary, part of the methylamine mixture to a catalytic reaction.

By reducing the quantity of TMA in the recycled methylamine mixture in the first step and by promoting the formation of DMA while suppressing the formation of TMA in the second step, the characteristic of the mordenite type zeolite catalyst, i.e., high selectivity for DMA can be satisfactorily achieved.

DETAILED DESCRIPTION

As conducive to a full understanding of the nature of this invention and of the points on which it is distinctly different from the prior art, an example of a known process will first be briefly described.

Figure 1:
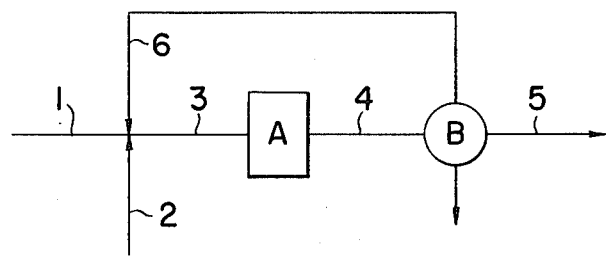
FIG. 1 is a flow sheet indicating the essential steps in the production of methylamines by a known process.

In the conventional method shown in FIG. 1, starting-material ammonia supplied via a line 1 is fed into a reaction tower A via a line 3, together with starting-material methanol supplied via a lin 2 and a methylamine-non-reacted ammonia mixture after being separated from the product amines (particularly, DMA), which mixture is supplied via a line 6. The reaction product is fed to a refining process (B) via a line 4. The product amines (particularly, DMA) are recovered via a line 5, and the separated other amines and non-reacted ammonia are transferred to the reaction tower A via the line 6.

Figure 2:
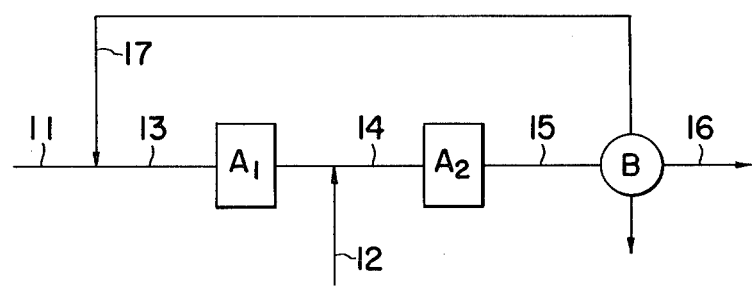
FIG. 2 is a flow sheet indicating the essential steps of a specific example of production of methylamines according to this invention.

In contrast to this conventional method, in accordance with the process of the present invention shown in FIG. 2, starting-material ammonia supplied via a line 11 and a methylamine mixture containing TMA and also the non-reacted ammonia after being separated from the product amines (particularly, DMA), which mixture is supplied via a line 17, are fed into a first reaction tower $A_1$ via a line 13. The first product from the first reaction tower $A_1$ is fed, together with starting-material methanol supplied via a line 12, into a second reaction tower $A_2$ via a line 14. The second product from the second reaction tower $A_2$ is fed into a refining process B via a line 15. The product amines (particularly, DMA) are recovered via a line 16, and the separated other amines, i.e., methylamine mixture containing TMA, and also the non-reacted ammonia are transferred to the first reaction tower $A_1$ via the line 17.

Figure 3:
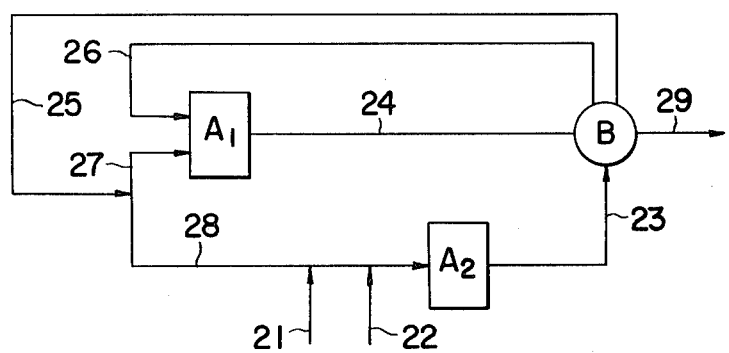
FIG. 3 is a flow sheet indicating the essential steps of another specific example of practice of this invention.

FIG. 3 is a flow sheet indicating another embodiment of the present invention.

The process of the present invention can be carried out according to the embodiment thereof shown in FIG. 3 in order to alleviate the load of the first step requiring an external supply of heat because of its endothermic reaction. That is, a part of the methylamine mixture containing TMA and also the non-reacted ammonia, and TMA alone after being separated from the product amines (particularly, DMA) are fed into the first reaction tower $A_1$ via a line 25 and then, a line 27 and a line 26, respectively. The first product from the first reaction tower $A_1$ is fed into the refining tower B via a line 24. The major portion of the methylamine mixture containing TMA and also the non-reacted ammonia from which DMA has been recovered and which has been subjected to other treatments, i.e., the residual methylamine mixture remaining after being fed into the first reaction tower $A_1$, is fed via the line 25 and then, a line 28 into the second reaction tower $A_2$ together with starting-material ammonia supplied via a line 21 and starting-material methanol supplied via a line 22. The second product from the second reaction tower $A_2$ is fed into the refining tower B via a line 23. In the refining tower B, the product amines (particularly, DMA) are recovered via a line 29, while the separated other amines, i.e., methylamine mixture containing TMA and also the non-reacted ammonia, and TMA alone are transferred to the first and second reaction towers $A_1$ and $A_2$, as described hereinabove.

The flow sheets shown in FIGS. 2 and 3 indicate most preferable embodiments of the present invention. However, the process of the present invention can be variously modified. For details, reference may be made to the following description.

1. FIRST STEP (1) Purpose

The purpose of this step is to react ammonia with a methylamine mixture containing TMA until an approximate equilibrium is reached, thereby to consume the TMA. That is, the reaction intended in this step is the conversion of TMA to DMA or MMA due to the reaction of ammonia with TMA, that is, a disproportionation reaction.

(2) Reactants

The methylamine mixture containing TMA which is one of the reactants is ordinarily a TMA-MMA mixture obtained by separating DMA from the product resulting from the DMA synthesizing step, namely the second step which will be described in detail hereinafter. The TMA-containing methylamine mixture may contain the non-reacted ammonia remaining in the second step as described hereinabove.

Another reactant for the first step is ammonia. At least part of the ammonia to be used throughout the first and second steps is used in the first step. In this case, the ammonia may be ammonia contained in the methylamine mixture or ammonia as a supplement to the ammonia consumed throughout all steps.

If necessary, part of the methanol to be used throughout all steps may be used for reaction with ammonia in the first step. It is preferable, however, that the total amount of the methanol be used for reaction with ammonia in the second step.

Ordinarily, the reactants, namely methanol, ammonia and TMA-containing methylamine mixture, should be suitably divided into a feed for the first step and a feed for the second step in such a ratio that the consumption of TMA under the reaction equilibrium is attained in the first step. The minimum requirement for the division of the reactants into the two feeds is that the ratio of the number of nitrogen atoms/the number of a carbon atoms (hereinafter referred to as N/C) in the first reaction region be the N/C in the TMA molecule (i.e., $\frac{1}{3}$) or more. Practically, it is desirable to divide the reactants so that the N/C in the first reaction region will be 50% or more, preferably, 90% or more, of the N/C in the total reactants (the sum of the feed for the first step and the feed for the second step).

(3) Catalyst

The catalyst for the first step may be any catalyst capable of promoting the formation of DMA or MMA to an equilibrium state by disproportionation reaction of TMA with ammonia. This catalyst may be one capable of promoting the formation of methylamines by dehydration reaction between methanol and ammonia. Such a catalyst can be generally selected from the group consisting of porous solid acid catalysts.

Because the first step mainly aims at converting TMA to DMA or MMA, it is preferable that the catalyst for the first step have a large average pore size. Porous solid acid catalysts comprising mainly silica and/or alumina, for example, silica, alumina such as γ-alumina, silica-aluminia, Y-type zeolite, X-type zeolite and the like, are preferable examples for use in the first step. These porous solid acid catalysts have an average pore size or effective pore size of the order of 9 to 100 Å (angstrom).

(4) Reaction condition

The first step is carried out under the reaction conditions of a reaction temperatue of from about 350° to 450° C. and a reaction pressure of from about normal pressure to 25 Kg/cm².G.

A continuous reaction mode using a fixed catalyst bed is ordinarily used. It is to be understood, however, that other reaction modes may be used.

2. SECOND STEP (1) Purpose

The main purpose of the second step is to synthesize methylamines, more DMA and less TMA than equilibrium values, by the dehydration reaction of methanol with ammonia or MMA.

DMA is recovered from the product resulting from the second step, and simultaneously the TMA-containing methylamine mixture to be fed to the first step is obtained.

(2) Reactants

The reactants comprise all or part of the product resulting from the first step, the residual methanol and ammonia from the first step and, if necessary, the TMA-containing methylamine mixture. The quantity of the methanol to be fed to the second step is 80% or more of the total quantity of methanol used.

The product from the first step is ordinarily used as an as-received product from the exit of the first step. If necessary, this product may be subjected to a moisture-removing procedure, a DMA-recovering procedure, and other treatments before it is used as the reactant. A mixture of methylamines other than DMA which is produced in the second step may be returned to the first step, as required.

With regard to the division of the reactants into the feed for the first step and the feed for the second step, reference may be made to the description of the first step.

(2) Catalyst

The catalyst for the second step should have a relatively small effective pore size. Generally, porous solid acids having an effective pore size of from 3 to 8 Å, preferably, from 3 to 7 Å, more preferably, from 4 to 6 Å, are desirable as the catalyst.

Examples of the catalyst for the second step are natural zeolites such as mordenite, clinoptilolite, erionite, ferrierite, laumonite, phillipsite, analcite and chabasite and various synthetic zeolites. Preferable catalysts are those comprising mainly a mordenite-type zeolite.

A representative example of the mordenite-type zeolite is a naturally occurring mordenite. The naturally occurring mordenite is of the following formula and contains a small quantity of rock crystal, montmorillonite or the like as an impurity:

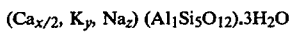

$(Ca_{x/2}, K_y, Na_z)(Al_1Si_5O_{12}).3H_2O$ wherein $x+y+z=1$, x/2, y and z represent, independently from each other, a number of from 0.1 to 0.6.

Although the values of x, y and z and the type and quantity of the impurities are somewhat variable depending on the place of origin, the mordenites of the above-mentioned formula are all porous solid acids having an effective pore size of about 5 Å.

A representative example of the mordenite type zeolite is a synthetic small port mordenite. The synthetic mordenite can be prepared by crystallizing $Na_2O.Al_2O_3.nSiO_2$ $(8<n<13)$ under hydrothermal conditions (J. Chem. Soc. 1948, 2158). The Na type zeolite obtained by this method often exhibits a relatively low activity. However, if a part of the sodium ions in the Na type zeolite is replaced by a hydrogen ion or di- and/or tri-valent ions such as calcium ion, the resulting zeolite can exhibit a high activity.

Examples of X-ray diffraction patterns characteristic of these mordenites are indicated in the following tables.

TABLE 1

| Relatively pure natural mordenite | | | |
|---|---|---|---|
| d(A) | I/Io | d(A) | I/Io |
| 2.51 | 40 | 4.00 | 80 |
| 2.89 | 60 | 4.53 | 60 |
| 3.22 | 90 | 6.60 | 50 |
| 3.39 | 80 | 9.11 | 50 |
| 3.48 | 100 | | |
| 3.84 | 40 | | |

TABLE 2

| Natural mordenite containing rock crystal | | | |
|---|---|---|---|
| d(A) | I/Io | d(A) | I/Io |
| 2.51 | 40 | 3.98 | 80 |
| 2.89 | 60 | 4.27 | 60 |
| 3.22 | 90 | 4.53 | 60 |
| 3.34 | 100 | 6.55 | 50 |
| 3.39 | 70 | 9.11 | 60 |

TABLE 2-continued

| Natural mordenite containing rock crystal | | | |
|---|---|---|---|
| d(A) | I/Io | d(A) | I/Io |
| 3.48 | 100 | | |

TABLE 3

| Synthetic mordenite | | | |
|---|---|---|---|
| d(A) | I/Io | d(A) | I/Io |
| 2.50 | 50 | 4.55 | 70 |
| 2.87 | 60 | 5.76 | 60 |
| 3.21 | 80 | 6.54 | 60 |
| 3.38 | 80 | 9.03 | 80 |
| 3.46 | 100 | | |
| 3.99 | 90 | | |

(3) Reaction condition

The second step is carried out under the reaction conditions of a reaction temperature of from about 280° to 450° C. and a reaction pressure of from about sealevel atmospheric pressure to 25 Kg/cm$^2$.G.

(4) Recovery of DMA and methylamine mixture containing TMA

The product resulting from the second step is not substantially different from a product resulting from the conventional process for synthesizing methylamines except that it contains a high content of DMA and a low content of TMA. Therefore, recovery of DMA and the TMA-containing methylamine mixture to be transferred to the synthesizing process from the second product can be accomplished by a conventional method, for example, such as that described in *Fluid Handling*, January, 1963, pages 13–14 and Japanese Patent Publication No. 34790/1980.

More specifically, in accordance with the former conventional method, the product from the second step is subjected to a continuous separating and refining procedure by means of four distillation columns. In the first column, removal of ammonia from the product is first carried out. In the second column, TMA is distilled out from the top of the column after water is poured into the column to suppress the azeotropy. Then, in the third column, the resulting product is dehydrated, and, finally, in the fourth column, MMA and DMA are distilled out from the top and bottom of the column, respectively. Thus, each methylamine is recovered. Ammonia from the first column, TMA from the second column and MMA from the fourth column are recovered as the TMA-containing methylamine mixture to be transferred to the synthesizing process.

In accordance with the latter method, the product from the second step is subjected to a continuous separating and refining procedure by means of three distillation columns. In the first column, ammonia, MMA, and a part of TMA are first distilled out as an azeotropic mixture. Then, in the second column where water extraction is effected, the remaining TMA is distilled out from the top of the column. Finally, in the third column, the residual product is dehydrated to recover DMA. The azeotropic mixture comprising ammonia, MMA, and TMA, which was obtained from the first column, and TMA from the second column are recovered as the TMA-containing methylamine mixture as in the former method.

The composition of the methylamine mixture is variable depending on the reaction conditions, the percentage of recovery of each methylamine as a commercial product, and the separating and refining conditions. In general, the methylamine mixture comprises 30 to 80% by weight of ammonia, 5 to 40% by weight of MMA, 5% by weight or less of DMA, and 10 to 60% by weight of TMA.

4. EXPERIMENTAL EXAMPLES

Comparative Example 1

A mixture of the components indicated in Line No. 3 of Table 4 was passed over 1 m$^3$ of a conventional catalyst comprising silica-alumina particles having a size of about 5 mm and an average pore size of 60 Å, at a temperature of 400° C. and a pressure of 20 atmospheres. A product mixture as indicated in Line No. 4 was obtained.

TABLE 4

| | Quantity of material passing through each line, Kg/hr | | | | | |
|---|---|---|---|---|---|---|
| Line No.* | 1 | 2 | 3 | 4 | 5 | 6 |
| Ammonia | 117 | 0 | 1356 | 1239 | 0 | 1239 |
| MMA | 0 | 0 | 287 | 308 | 21 | 287 |
| DMA | 0 | 0 | 19 | 282 | 263 | 19 |
| TMA | 0 | 0 | 485 | 506 | 21 | 485 |
| Methanol | 0 | 436 | 436 | 6 | 6 | 0 |
| Water | 0 | 0 | 0 | 241 | 241 | 0 |
| Total | | | 2583 | | | 2030 |

*FIG. 1

Comparative Example 2

The mixture having the same ratio of the number of nitrogen atoms to the number of carbon atoms (herein referred to as N/C) as that of the reaction mixture of Comparative Example 1 and having the composition indicated in Line No. 3 of Table 5, was passed over 1 m$^3$ of a natural mordenite Ca$_{0.27}$K$_{0.14}$Na$_{31}$Al$_1$Si$_5$O$_{12}$.3-H$_2$O (effective pore size: about 5 Å) exhibiting the X-ray pattern shown in Table 1 under the same conditions as those described in Comparative Example 1. A product as indicated in Line No. 4 was obtained.

TABLE 5

| | Quantity of material passing through each line, Kg/hr | | | | | |
|---|---|---|---|---|---|---|
| Line No.* | 1 | 2 | 3 | 4 | 5 | 6 |
| Ammonia | 117 | 0 | 1188 | 1071 | 0 | 1071 |
| MMA | 0 | 0 | 286 | 307 | 21 | 286 |
| DMA | 0 | 0 | 19 | 282 | 263 | 19 |
| TMA | 0 | 0 | 370 | 391 | 21 | 370 |
| Methanol | 0 | 435 | 435 | 6 | 6 | 0 |
| Water | 0 | 0 | 0 | 241 | 241 | 0 |
| Total | | | 2298 | | | 1746 |

*FIG. 1

Example 1

A mixture of the components indicated in Line No. 13 of Table 6 was passed over 0.3 m$^3$ of a conventional catalyst comprising silica-alumina particles having a size of about 5 mm and an average pore size of 60 Å, at a temperature of 375° C. and a pressure of 20 atmospheres.

439 Kg/hr of methanol was added to the resulting product to prepare a mixture having the same N/C value as the reaction mixture of Comparative Example 1 and the composition indicated in Line No. 14 of Table 6. The resulting mixture was passed over 1 m$^3$ of the same mordenite as specified in Comparative Example 2 under the same conditions as those described in Comparative Example 2. A reaction product having the composition indicated in Line No. 15 of Table 6 was obtained.

TABLE 6

| Line No.* | Quantity of material passing through each line, Kg/hr | | | | | | |
|---|---|---|---|---|---|---|---|
| | 11 | 12 | 13 | 14 | 15 | 16 | 17 |
| Ammonia | 117 | 0 | 1001 | 1024 | 885 | 0 | 885 |
| MMA | 0 | 0 | 294 | 188 | 315 | 21 | 294 |
| DMA | 0 | 0 | 19 | 144 | 282 | 263 | 19 |
| TMA | 0 | 0 | 236 | 194 | 257 | 21 | 236 |
| Methanol | 0 | 439 | 0 | 439 | 10 | 10 | 0 |
| Water | 0 | 0 | 0 | 0 | 241 | 241 | 0 |
| Total | | | | 1989 | | | 1434 |

*FIG. 2

Example 2

Each of mixtures of the compositions indicated in Line Nos. 27 and 26, respectively, of Table 7 was passed over 0.1 m$^3$ of a conventional catalyst, comprising $\gamma$-alumina particles of a size of 5 mm and an average pore size of 46 Å, at a temperature of 400° C. and a pressure of 18 atmospheres. The resulting product was transferred to the refining step B. 116 Kg/hr of ammonia and 462 Kg/hr of methanol were added to a mixture having the composition indicated in Line No. 28 which was separated from the product. The resulting mixture was passed over 1.5 m$^3$ of a natural mordenite $Ca_{0.22}K_{0.30}Na_{0.26}Al_1Si_5O_{12}.3H_2O$ (effective pore size of about 5 Å) in which about 80% of the cations were replaced by hydrogen ions, and which exhibited the X-ray diffraction pattern shown in Table 2, at a temperature of 300° C. and a pressure of 18 atmospheres. A reaction product having the composition indicated in Line No. 29 was obtained.

TABLE 7

| Line No.* | Quantity of material passing through each line, Kg/hr | | | | | | | | |
|---|---|---|---|---|---|---|---|---|---|
| | 21 | 22 | 23 | 24 | 25 | 26 | 27 | 28 | 29 |
| Ammonia | 116 | 0 | 1140 | 52 | 1192 | 0 | 56 | 1136 | 0 |
| MMA | 0 | 0 | 214 | 16 | 209 | 0 | 10 | 199 | 21 |
| DMA | 0 | 0 | 265 | 19 | 23 | 0 | 2 | 21 | 261 |
| TMA | 0 | 0 | 95 | 33 | 59 | 49 | 3 | 56 | 69 |
| Methanol | 0 | 462 | 37 | 0 | 0 | 0 | 0 | 0 | 37 |
| Water | 0 | 0 | 239 | 0 | 0 | 0 | 0 | 0 | 239 |
| Total | 116 | 462 | 1990 | 120 | 1483 | 49 | 71 | 1412 | 627 |
| N/C | | | 3.3 | 1.5 | | | | | |

*FIG. 3.

In general, in order to alleviate the load of the first step requiring external supply of heat because of its endothermic reaction, the method described in Example 2, for example, can be utilized. By selecting the reaction conditions, for example, by reducing the reaction temperature to about 300° C., the ratio of formation of TMA can be further reduced. When the process as shown in FIG. 3 is carried out under such reaction conditions, the scale of the first step can be reduced to a remarkable extent.

That is, in the case where the starting materials methanol and ammonia and a part of the methylamine mixture are reacted together in the second step, the resulting product (23) has a remarkably lower content of TMA than that in the conventional method. Therefore, the quantity of the materials (25,26) to be recycled into the first step inlet or the second step inlet from the second step together with a part of the product from the first step, and the quantity of the TMA to be dispropor-tionated in the first step can be reduced, which results in a remarkable reduction in the load of the first step.

We claim:

1. In a process for enhancing production of dimethylamine, wherein methanol, ammonia and a methylamine mixture containing trimethylamine are subjected to a gas phase catalytic reaction, and wherein said methylamine mixture has been produced in said process, the improvement which comprises conducting the gas phase catalytic reaction in two steps, the first step comprising subjecting the methylamine mixture containing trimethylamine and ammonia to a catalytic reaction in the presence of a porous solid acid catalyst having an average pore size or effective pore size of from 9 to 100 Å and selected from the group consisting of silica, $\gamma$-alumina, silica-alumina, Y-type zeolite and X-type zeolite thereby to reduce the quantity of the trimethylamine, at a temperature of 350° to 450° C. with a ratio of the number of nitrogen atoms to the number of carbon atoms (N/C) of the reactants of at least $\frac{1}{3}$, the second step comprising subjecting at least a part of the product resulting from the first step and methanol to a catalytic reaction in the presence of ammonia and in the presence of a crystalline aluminosilicate catalyst having an effective pore size of 3 to 8 Å thereby to produce more dimethylamine.

2. The process as claimed in claim 1 wherein said first step is conducted in the presence of 0 to 20% by weight of methanol, the percentage being based on the total quantity of methanol used in the first step and the second step.

3. The process as claimed in claim 1 said methylamine mixture is one which is obtained from the product from the second step.

4. The process as claimed in claim 1, wherein said methylamine mixture is one which is obtained from the products from the first and second steps.

5. The process as claimed in claim 1 wherein said second step is conducted in the presence of the methylamine mixture containing trimethylamine.

6. The process as claimed in claim 1 wherein said porous solid acid catalyst having an average pore size or an effective pore size of 9 to 100 Å is selected from; silica, alumina, silica-alumina, and said crystalline aluminosilicate having an effective pore size of 3 to 8 Å is selected from a mordenite type zeolite.

7. In a process for enhancing production of dimethylamine, wherein methanol, ammonia and a methylamine mixture containing trimethylamine are subjected to a gas phase catalytic reaction, and wherein said methylamine mixture has been produced in said process, the improvement which comprises conducting the gas phase catalytic reaction in two steps, the first step comprising subjecting the methylamine mixture containing trimethylamine and ammonia to a catalytic reaction in the presence of a porous solid acid catalyst having an average pore size or effective pore size of from 9 to 100 Å and selected from the group consisting of silica, $\gamma$-alumina, silica-alumina, Y-type zeolite and X-type zeolite at a temperature of 350° to 450° C. with a ratio of the number of nitrogen atoms to the number of carbon atoms (N/C) of the reactants of at least $\frac{1}{3}$, to convert trimethylamine to dimethylamine, monoethylamine or a mixture thereof by reaction of ammonia with trimethylamine, and the second step comprising subjecting at least a part of the product resulting from the first step and methanol to a catalytic reaction in the presence of ammonia and in the presence of a crystalline aluminosilicate catalyst having an effective pore size of 3 to 8 Å, thereby to produce more dimethylamine and less trimethylamine than equilibrium values.

8. The process as claimed in claim 6 wherein said porous solid acid catalyst for the first step is selected from a member of the group consisting of γ-alumina, Y-type zeolite and X-type zeolite.

9. The process as claimed in claim 6 wherein said crystalline aluminosilicate catalyst for the second step has an effective pore size of 3 to 7 Å.

10. The process as claimed in claim 6 wherein said crystalline aluminosilicate catalyst for the second step has an effective pore size of 4 to 6 Å.

* * * * *